United States Patent [19]

Neufeld

[11] 4,103,683
[45] Aug. 1, 1978

[54] SUB-TROCHANTERIC NAIL

[76] Inventor: John A. Neufeld, 10,000 SE. Main, Suite 402, Portland, Oreg. 97216

[21] Appl. No.: 803,347

[22] Filed: Jun. 3, 1977

[51] Int. Cl.² ............................ A61F 5/04; A61B 17/18
[52] U.S. Cl. ............................. 128/92 BA; 128/92 BC; 128/92 EB; 128/92 EC
[58] Field of Search ......... 128/92 BA, 92 BB, 92 BC, 128/92 R, 92 B, 92 E, 92 EB, 92 EC, 92 G, 83

[56] References Cited

U.S. PATENT DOCUMENTS

| | | | |
|---|---|---|---|
| 2,239,088 | 4/1941 | Ettinger | 128/92 BA |
| 3,025,853 | 3/1962 | Mason | 128/92 BA |
| 3,433,220 | 3/1969 | Zickel | 128/92 BC |
| 3,486,500 | 12/1969 | Ball et al. | 128/92 BA |
| 3,709,218 | 1/1973 | Holloran | 128/92 BC X |

FOREIGN PATENT DOCUMENTS

| | | | |
|---|---|---|---|
| 2,288,506 | 5/1976 | France | 128/92 BC |
| 757,951 | 11/1953 | Fed. Rep. of Germany | 128/92 BC |

*Primary Examiner*—Ronald L. Frinks
*Attorney, Agent, or Firm*—Cushman, Darby & Cushman

[57] ABSTRACT

A surgical appliance for stabilizing a fractured thighbone is shown having a femoral nail for insertion in the medullary canal and a crosspiece supported at one end in a slot that extends longitudinally lengthwise in the femoral nail, the other end of the crosspiece being bedded in the femoral head. The crosspiece is formed as a flat, spirally shaped element that slides through the slot in the femoral nail when it is seated in the medullary canal and the fracture has been reduced, the leading end of the crosspiece being driven through the neck and into the femoral head. The assembled nail and crosspiece arrangement provides a rigid elongated cross sectional area of the crosspiece supported in the slot in the femoral nail and a flat leading end that serves as a bearing surface in the femoral head that is turned at about a right angle with respect to the slot in the nail whereby to minimize cutting out of the leading end of the crosspiece through the wall of the femoral head. The crosspiece and the femoral nail may both be cannulated to simplify the process of insertion and the femoral nail may be curved slightly to match the normal anterior bow of the thighbone.

10 Claims, 8 Drawing Figures

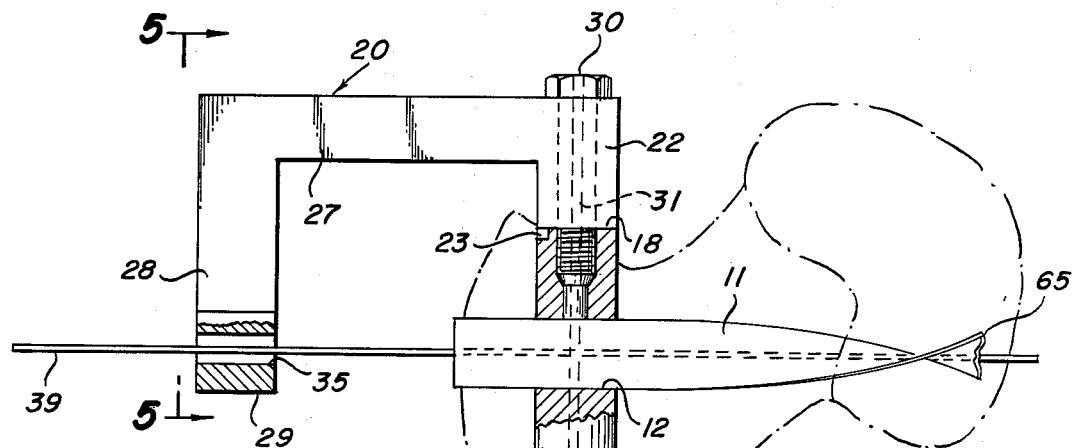
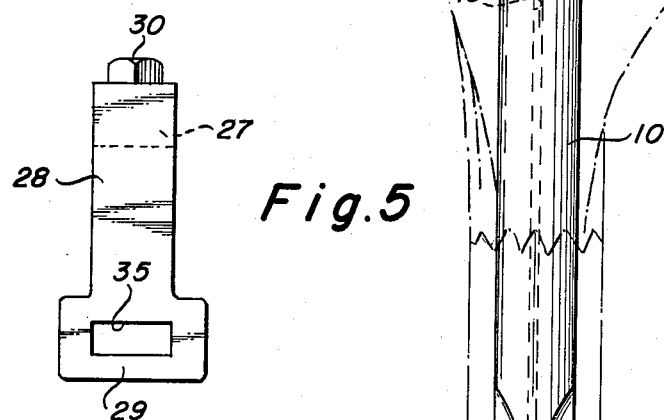
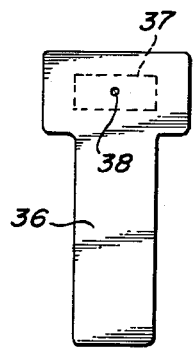
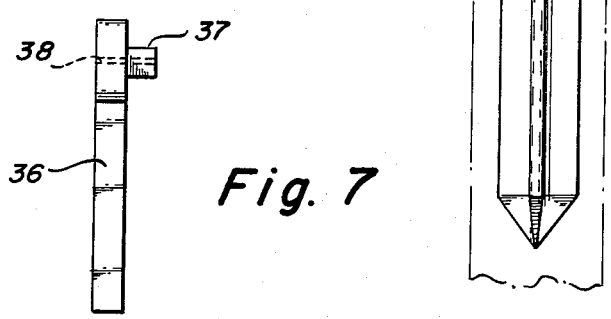

SUB-TROCHANTERIC NAIL

BACKGROUND

The use of nails to stabilize fractured thighbones has been practiced for some time as discussed in and taught by the improvements covered in the U.S. Pat. No. 3,433,220 to Zickel, Mar. 18, 1969 and U.S. Pat. No. 3,025,853 to Mason, Mar. 20, 1962. The Zickel patent shows a femoral rod or nail adapted to be inserted in the medullary canal of a thighbone to extend from the trochanter down the thighbone past the fractured area and into the distal portion of the fractured bone. After the fracture has been reduced, the femoral nail may be inserted while the reduction is maintained with suitable bone clamps and then when using the Zickel rod, a cross nail is driven through a tunnel in the femoral rod through the neck and into the head of the femur. The Zickel nailing appliance provides a pair of rods each one being especially shaped to fit either the right or left leg thighbone, thus requiring two differently shaped nails or rods having an enlarged head and specific shape to accommodate a crosspiece that must have a substantial diameter to support the cross bending forces transmitted between the femoral nail and crosspiece placed in the fractured bone while the patient recovers and the fracture heals.

In use, the Zickel nail requires that there be a precision fit between the crosspiece and the tunnel in the rod in order to properly insert the crosspiece in the femoral head. It may be necessary during the course of an operation to remove and reset the rod in a more precise position by extracting it from its position in the medullary canal after having embedded its enlarged head in the trochanter. The femoral rod is directed into such a position by means of its temporarily attached tunnel locator tool and when the rod has been turned to a new position, the rod is again driven into the medullary canal with an added possibility of slightly displacing some additional fragments of the fractured bone while enlarging the displacement of tissue in the greater trochanter as the enlarged head is driven home. The degree of change of rotation or depth of insertion of the Zickel rod may not be great but each manipulation requires the time and expert attention of the surgeon and carries with it the possibility of further damage resulting from the reinsertion process.

BRIEF DESCRIPTION OF THIS INVENTION

The femoral nail of this invention provides an improvement on the known structures provided for the surgeon's use. The herein disclosed nail preferably has a slim and uniform cross sectional configuration that may be placed in the bone with the required degree of precision needed while minimizing the possibility of damage to the normal tissue of the greater trochanter, the medullary canal and the femoral head. The nails are formed to have cylindrical bodies of a desired uniform diameter for the size of thighbone and type of fracture to be treated, and may be curved slightly to match the normal bow of the thighbone to provide thighbone nails that are interchangeable between the right and left legs.

This femoral nail has a longitudinally extending slot therethrough that is adapted to receive and support a crosspiece disposed at about a right angle with respect to the longitudinal axis of the nail. The crosspiece is formed as a flat strip twisted to a spiral shape with a section having a length equal to one quarter of a full turn of the strip forming the crosspiece that extends from the slot in the nail, through the trochanter, the neck and into the femoral head with the leading end of the crosspiece embedded in the wall of the femoral head. The slot has a cross sectional area to snugly receive the flat strip and the side walls of the slot are arcuately shaped to permit the position of the crosspiece to be changed through a range of positions from anterior, neutral or posterior around the longitudinal axis of the femoral nail without requiring the withdrawal and resetting of the nail.

Due to the spiral shape of the crosspiece, the flat free end of the crosspiece is turned as it moves toward the femoral head to be lodged in the wall of the head in a position that distributes the forces in a way to minimize cutting out of the free end. It will be noted that when the crosspiece is in assembled relation with the femoral nail and has its free end lodged in the femoral head, that the planar faces of the width of the nail are parallel with the axis of the nail at the intersection of the crosspiece and the nail to provide a maximum crosspiece dimension at the junction to support the bending moment developed at said junction between these elements.

Another object is to provide a femoral nail design having more general utility whereby to minimize inventory problems.

It is therefore an object of this invention to provide an improved sub-trochanteric fracture appliance.

Another object is to provide a femoral nail that may be inserted in the medullary canal and trochanter of a fractured thighbone with less risk of damage thereto.

Another object of the invention is to provide an improved slim design of femoral nail and crosspiece assembly for a sub-trochanteric fracture appliance adapted to be inserted in the thighbone with a minimum of disturbance of the bone structure.

Another object is to provide a crosspiece for a femoral nail having a maximum dimension at the junction between the nail and crosspiece for absorbing bending forces.

Another object is to provide a crosspiece supported by a femoral nail, the crosspiece having a maximum bearing pad at its free end to be embedded in the wall of the femoral head to minimize the possible cutout of the crosspiece from the wall.

Another object is to provide a crosspiece supported at a right angle relative to the longitudinal axis of the femoral nail in a sub-trochanteric fracture appliance.

Another object is to provide a femoral nail and crosspiece combination in a sub-trochanteric fracture appliance that can be used in either a right or left thighbone.

Another object is to provide a femoral nail and crosspiece for a sub-trochanteric fracture appliance that may be assembled with the crosspiece in one of several radial angular positions about the longitudinal axis of the femoral nail to avoid the necessity for withdrawal of a nail and replacement in the medullary canal when minor adjustment of the anterior or posterior position of the crosspiece relative to the nail is needed.

Another object is to provide a femoral nail and crosspiece combination for a sub-trochanteric fracture appliance in which both of the elements to be assembled together may be cannulated for aiding their placement over their respective guide wires that may be initially set with the aid of modern fluoroscopic techniques.

These and other objects will appear more fully from the specification below.

IN THE DRAWINGS

FIG. 1 is a front view of the femoral nail, the crosspiece and the driver and slot locator of the subtrochanteric fracture appliance assembled together with a fractured thighbone showing the nail extending from the greater trochanter into the medullary canal in the distal portion of the thighbone;

FIG. 5 is a side view looking along line 5—5 of FIG. 1 showing the slot locator portion of the removable driver means for the appliance;

FIG. 6 is a side elevation of a wire guide tool adapted for use with the aperture in the slot locator;

FIG. 7 is a front view of the wire guide shown in FIG 6; and

DETAILED DESCRIPTION

The femoral nail and crosspiece forming the subtrochanteric fracture appliance has a particular utility for stabilizing thighbone fractures in the upper thighbone or subtrochanteric region. It includes a femoral nail 10 that is designed to be inserted in the medullary canal to stabilize the distal portion of a fractured thighbone in proper alignment with the trochanter and femoral head of the bone while healing of the fracture takes place. The femoral nail is adapted to be assembled with a crosspiece 11 that is slidingly supported in a narrow slot 12 in the nail while the crosspiece is driven through the trochanter, the neck and into the femoral head to have its free end lodged in the bony wall of the femoral head. The crosspiece provides the main stabilizing support for the femoral nail 10 to prevent it from rotating or twisting about its longitudinal axis in order to prevent any displacement of the trochanter relative to the distal portion of the thighbone that might be occasioned by a bending moment that could not otherwise be absorbed by the nail alone without a possible displacement thereof. Both the femoral nail 10 and the crosspiece are cannulated or provided with central passages extending longitudinally therethrough for a purpose that will appear more fully below.

Figure 4:
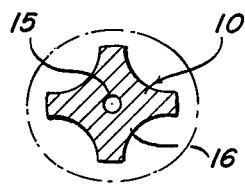
FIG. 4 is a sectional view of the thighbone nail taken on line 4—4 of FIG. 1.

The nail 10 and crosspiece 11 are adapted to be positioned in the assembled relationship shown in FIG. 1, to extend from the greater trochanter into the medullary canal, the placement of the nail and the cooperating crosspiece being accomplished by a procedure generally well known to surgeons. Briefly, the process for making use of this sub-trochanteric fracture appliance requires that the patient, after being prepared for the operation, be placed on an operating table so that the surgeon may make a short incision to expose the side and top portion of the trochanter only in order to decrease the distal exposure when making closed nailings. An opening is then made in the top of the greater trochanter through which a guide wire may be inserted and the medullary canal can be reamed. Using any known x-ray method but preferably the modern fluoroscopic methods, the fracture can be reduced by traction and manipulated by an assistant if necessary while the guide wire is inserted to further align the trochanter and distal portions of the fractured thighbone after which the medullary canal can be reamed and nail 10 can be inserted into the canal. Preferably the cannulated nail having the passage 15 therethrough is guided into the canal by means of the guide wire to direct the nail properly into the medullary canal. The lower portion of the nail may be scalloped as at 16, referring to FIG. 4 to provide more surface area of contact to engage the nail more solidly in the distal portion of the fractured thighbone. Other shapes, such as triangular, semi-tubular, diamond, or cloverleaf, might also be used.

Figure 8:
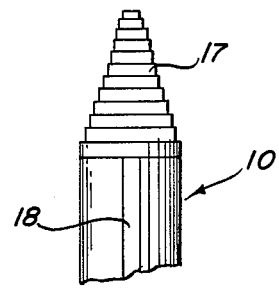
FIG. 8 is a detail side elevation of a reamer attached to the nail that may be used when a retrograde nail fitting technique is used.

In those situations where an incision to made at the fracture site and is continued upwardly above the trochanter along the posterior border of the trochanter, the nail can be fitted to the trochanter using a retrograde procedure. When this course is followed before the fracture is reduced, the medullary canal of the distal shaft of the fractured femur is first reamed and the nail 10 is fitted into the shaft and then extracted. The proximal or trochanteric fragment is then reamed with progressively larger reamers in a retrograde manner through the medullary canal and out the tip of the greater trochanter. A reamer 17, like that shown in FIG. 8, can be mounted at the thread upper end 18 of passage 15 on nail 10. The reamer is formed with a plurality of reaming shoulders to gradually enlarge the medullary canal to receive the nail and after the trochanter has been reamed, the nail that has been used as the reamer is withdrawn from the trochanter and then the fracture can be reduced as above described and a guide wire inserted to align the trochanter and distal portions of the fractured bone to be supported on the nail that may then be placed in the bone.

Figure 2:
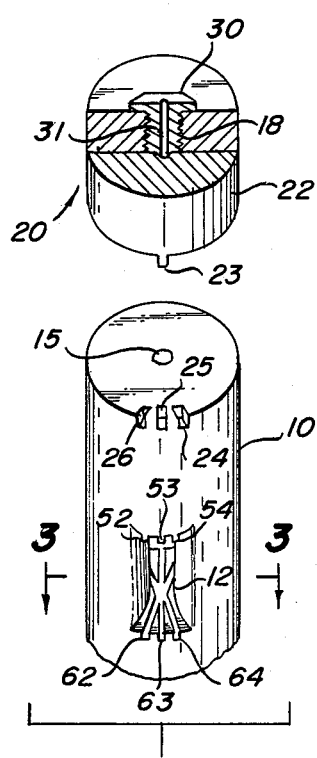
FIG. 2 is a perspective side view of a portion of the upper end of the femoral pin assembly of FIG. 1, showing the upper end of the femoral pin and its slot structure and the end portion of a slot locator spaced from the upper end of the femoral nail, the end portion being partly broken away.

In order to drive the femoral nail into the reamed canal, whether reamed from the top of the trochanter or retrograde fitted, a driving tool and slot locator 20 shown in FIG. 1, is temporarily attached to the upper end of the nail by a mounting head 22 integral with the tool, the head having a locator tongue 23 that is adapted to cooperate with either one of the three keyways 24, 25 or 26 shown in FIG. 2, that are provided in the exposed end of the nail 10. The keyway, into which tongue 23 is fitted during assembly of the tool with the nail, fixes the position of the slot locator means of the tool radially with respect to the longitudinal axis of the nail 10. For this purpose, the tool includes a radially extending arm 27 integral with the head, the arm having a depending slot guide means 28 fixed thereto. The slot guide includes an enlarged head 29 having a slot 35 passing through it, the slot 35 in the slot locator being thus fixedly supported to be held in an exact spaced relation relative to slot 12 in nail 10. The driving tool is attached to the nail by a bolt 30 engaged in threads 18, the bolt having a longitudinal passage 31 therethrough that is aligned with passage 15. When the tool 20 has been bolted onto nail 10 with tongue 23 cooperating with the selected one of the keyways 24, 25 or 26, the nail 10 may be inserted into the reamed out medullary canal and a proper force applied to tool 20 to drive the nail into the canal. The position of slot 35 in the slot locator element of the tool determines how far the insertion is to be made and the relative rotation of the pin in the canal so that when slot 35 shows that the slot 12 in the nail is in a proper position to receive the crosspiece 11 for driving into the femoral head, insertion of the nail 10 into the reamed medullary canal is discontinued.

At this point in the operation, a wire guide means 36 shown in FIGS. 6 and 7, that has a rectangular bearing 37 integral therewith, is mounted in slot 35. The bearing 37 has a precision fit in slot 35 and the wire guide has an aperture 38 through it for receiving a guide wire 39, FIG. 1, that is driven into the femoral head by conventional procedures as the surgeon uses a fluoroscopic means and the wire guide to exactly locate the position of the wire that extends through slot 12 and into the femoral head in preparation for the insertion of the crosspiece.

Once the nail 10 has been driven into the reamed medullary canal, it is best to allow it to remain in place to avoid disturbance of the fracture site once the fracture has been reduced and nail 10 driven into place. This permits the nail to be inserted in a one-step procedure with the least possibility for displacement of bone fragments at the fracture site.

Figure 3:
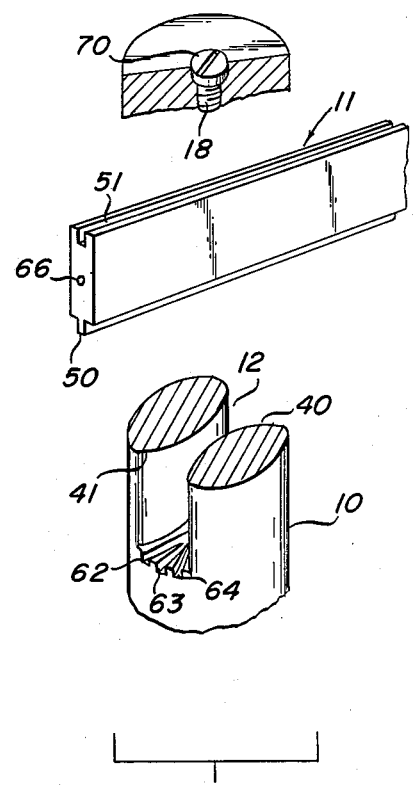
FIG. 3 is a three quarter detail perspective view taken on line 3—3 of FIG. 2, showing the crosspiece that is driven through the slot in the femoral nail for lodgment in the femoral head, the crosspiece being shown in a spaced away relationship to the slot through which it is designed to pass.

In some instances after the nail 10 has been driven, the placement of the guide wire for the crosspiece may indicate that there should be slight antiversion or retroversion of the prospective position of the crosspiece. To make such a change in position possible before the crosspiece is driven and without requiring the withdrawal and resetting of the nail 10, the slot 12 in the nail is provided with arcuately shaped side walls 40 and 41 best seen in FIG. 3. These side walls are aligned to be parallel with the longitudinal axis of the nail and when the tool 20 and its tongue 23 is lifted from slot 25 in which it is normally fitted for driving the nail into the reamed medullary canal, the tool 20 may be rotated anteriorly or posteriorly around the axis of the nail to engage tongue 23 in one of the other keyways 24 or 26, for example. The shape of side walls 40 and 41 in slot 12 permits the wire inserted through wire guide 36 to be rotated about the longitudinal axis of the nail to be driven into the femoral head in a different direction without removal of the nail 10 from the medullary canal.

After a proper positioning of the wire guide through centering guide 36 and slot 12 has been thus accomplished by repositioning the slot locator means relative to nail 10, the insertion of the crosspiece to slide through slot 12 may proceed. The appliance here shown makes use of a crosspiece 11 in the form of a flat spirally shaped rigid bar. The bar has a substantially rectangular cross section that has a height much longer than its width. The bar has a spiral formed on a pitch of about one revolution in 8 inches and each crosspiece is cut into a length that includes ¼ of a twist. The cross section of the crosspiece is designed to slidingly fit through slot 12 with the walls of slot 12 in tight bearing engagement with the periphery of the crosspiece. The crosspiece may additionally be formed on its narrow edges with a tongue 50, see the exploded view in FIG. 3, and groove 51 adapted to cooperate respectively with one of the grooves 62, 63 or 64 on one of the end walls of slot 12 and tongues 52, 53 and 54 on the other end wall of slot 12. The free end 65 of the crosspiece, see FIG. 1, is preferably configured to have a shape for cutting through the marrow and other substances filling the trochanter, and the neck and femoral head, as it is driven forwardly until its end is seated in the bone forming the wall of the head. The crosspiece is cannulated to have a passage 66 that extends longitudinally through it for cooperation with the guide wire 39 after the wire has been properly set in the desired position with the centering guide 36 as above described. When the crosspiece wire guide has been set, the wire guide 36 is removed and the cannulated crosspiece is mounted on the guide wire to be passed through the aperture 35 in the slot guide. The spiral shape of the crosspiece causes it to rotate as it passes longitudinally through aperture 35 and when the tip of the crosspiece reaches slot 12, the crosspiece passes into the slot with the tongue and groove elements 50 and 51 of the crosspiece in sliding contact with the cooperating pairs of tongue and groove elements 52 and 62, 53 and 63, or 54 and 64 in the end walls of the slot 12 as determined by the seating of tongue 23 in one of the respective keyways 24, 25 or 26. The precision alignment of the wire and the wire guide is established by positioning the key 23 in one of the keyways 24, 25 or 26 so that the slot locator aperture 35 and its associated guide wire centering tool 36 are accurately aligned in either a neutral or anteriorly or posteriorly turned position relative to slot 12 in nail 10 to ensure a perfect fit so that the crosspiece can be driven through slot 12 with the tongue and groove elements 50 and 51 sliding along their respective cooperating elements in slot 12, with which the crosspiece has a tight fit, until the free end 65 of the crosspiece is embedded in the bone forming the wall of the femoral head. The direction of movement of the crosspiece through the neck and into the head is initially controlled by the movement of the crosspiece through slot 35 in tool 20 and slot 12 in the nail. It will be noted that due to the interaction of the spiral shape as it passes through these slots 12 and 35, that the free end 65 of the crosspiece is turned to an ultimate position such that if the nail is considered to be vertical in FIG. 1, the free end seated in the bone wall at the femoral head is horizontal. When positioned in the nail in the manner shown, at the juncture of the crosspiece with the nail, the vertical position of the crosspiece in the slot 12 gives the crosspiece its longest dimension to absorb bending stresses where they are the greatest. Thus all of the forces exerted on the crosspiece are distributed over the area defined by the width of the crosspiece and the horizontal width of the free end thus minimizing the possible cutting out of the end 65 through the wall of the femoral head while positioning the crosspiece in the nail to best transmit bending forces from the crosspiece to be absorbed along the length of the nail.

The crosspiece intersects the nail at substantially right angles to the longitudinal axis of the nail thus permitting the slot 12 in the nail to be as near as possible to the opening in the greater trochanter that must be made for the insertion of the nail into the medullary canal. Since the second opening in the trochanter for receiving the crosspiece is near this first opening, only a relatively small incision need be made in the leg in order to place this sub-trochanter fracture appliance in position in the thighbone. Also, because the top of the nail and the crosspiece are firmly embedded in the walls of the trochanter and the horizontally disposed free end of the crosspiece is embedded in the bony wall of the femoral head, the appliance is firmly seated in place with all of the forces for supporting the fractured elements of the thighbone properly distributed as widely as possible. After the crosspiece has been driven into the femoral head, a set screw 70 shown in FIG. 3, may be screwed with the threaded end 18 of the nail to positively hold the crosspiece and nail in their assembled position.

After the fracture has healed, it is a simple procedure to reach the exposed end of crosspiece 11 to extract it from the femoral head and then nail 10 can be withdrawn from the medullary canal through the trochanter. The nail 10 preferably has a relatively slim cylindrical body having a constant diameter throughout its entire length with the narrow slot 12 formed therein near its upper end to receive the crosspiece and scalloped lower end 16. Since the crosspiece is aligned widthwise with the slot and is positioned vertically therein to best absorb bending stresses, it is seen that a relatively narrow nail may be used to do the job that has heretofore required a nail having a thicker head portion that tends to produce more damage in the trochanter when inserted in the fractured thighbone.

As above indicated, the nail of this invention has a slim, trim configuration that minimizes damage caused by driving the nail into the thighbone. The nail may be curved slightly to match the normal anterior bow of the thighbone. Since the nails are otherwise identical from side to side and end to end, any nail may be used in either a right or left thighbone. It is apparent that nails having different diameters may be provided. Heavier nails can be used for pathological fractures when required or thinner nails may be used when possible. The nail can be used without a crosspiece and the trochanter can be reamed in a retrograde manner if this is deemed to be the best procedure to follow in a particular case, making it possible to use this one design of nail in such a variety of situations that hospital inventories may be greatly decreased.

The structure and manner of using the preferred form of the sub-trochanteric fracture appliance of this invention has been fully set forth above. It is possible that modifications thereof may occur to others skilled in the art, that will fall within the scope of the following claims.

What is claimed is:

1. A sub-trochanteric fracture appliance for use in a surgical procedure for stabilizing the trochanter and distal portions of a fractured upper thighbone, the appliance including a crosspiece that may be assembled in combination with a universal right and left handed femoral nail, the nail being adapted for insertion in the medullary canal of the thighbone to extend from the trochanter into the distal portion of the bone and the crosspiece extending across the trochanter and into the neck and femoral head thereof, comprising a cylindrical femoral nail adapted to be inserted to extend for a substantial distance from the greater trochanter through the medullary canal into a distal portion of a fractured thighbone, said femoral nail having a narrow longitudinally extending slot near one end thereof defined by top and bottom walls and longitudinally aligned arcuate side walls, said slot being positioned lengthwise of said femoral nail to be situated opposite the femoral head of the thighbone when said nail is positioned in said trochanter and medullary canal with said slot traversing a portion of said trochanter, an elongated flat spirally designed crosspiece having a cross sectional shape that has an area of a size to just neatly fill the open area constituting said slot, said spiral of said crosspiece having a pitch in the order of one revolution in an 8-inch length, said crosspiece having a length equal to about ¼ a full twist of the spiral and being adapted to be inserted in said slot to be driven therethrough to extend through the neck of the femur and have one end firmly seated in said slot and its other end positioned generally horizontally and lodged in the femoral head of the thighbone.

2. An appliance as in claim 1 wherein said nail and said crosspiece are each cannulated to fit over a guide wire to guide the nail and crosspiece into their respective positions in the fractured thighbone.

3. An appliance as in claim 1 wherein said nail has a uniform outer periphery defined by a constant diameter.

4. An appliance as in claim 1 wherein said nail and said crosspiece are each cannulated to fit over a guide wire respectively to guide the nail and crosspiece into their ultimate positions in the fractured thighbone and said nail has a uniform outer periphery defined by a constant diameter.

5. An appliance as in claim 1 wherein said crosspiece has a beveled tip to be embedded in the bony wall of said femoral head.

6. An appliance as in claim 1 wherein one end of said slot is positioned close to the end of said nail at the trochanter and said end walls of the slot are disposed at right angles to the longitudinal axis of said nail.

7. An appliance as in claim 1 wherein at least one of said end walls of the slot has guide means therein for guiding the crosspiece to a selected position that is either neutral, anterior or posterior with respect to the longitudinal axis of the slot in the nail situated in the medullary canal.

8. An appliance as in claim 7 wherein one of said end walls has a plurality of grooves disposed at angles one relative to the other for guiding the crosspiece to said selected position, and said crosspiece having a tongue means integral with one edge thereof to engage in a selected one of said groove means.

9. An appliance as in claim 8 wherein the other of said end walls of said slot has a corresponding plurality of angularly disposed tongue guide means integral therewith, said tongue guide means on said other wall being positioned in complementary positions with respect to the groove guide means on said one end wall, and the other side edge of said crosspiece has a groove means formed therein whereby the tongue means and groove means on said side edges of said crosspiece cooperate with said selected ones of said pairs of complementary tongue and groove guide means.

10. An appliance as in claim 1 wherein said femoral nail is curved slightly throughout its length to match the normal anterior bow of the thighbone.

* * * * *